United States Patent [19]
Laidler

[11] 3,984,531
[45] Oct. 5, 1976

[54] TECHNETIUM-99m-TIN-MONOFLUOROPHOSPHATE COMPLEX

[75] Inventor: John Barry Laidler, Amersham, England

[73] Assignee: The Radiochemical Centre Limited, England

[22] Filed: Feb. 15, 1974

[21] Appl. No.: 442,902

[30] Foreign Application Priority Data
Mar. 14, 1973  United Kingdom............... 12320/73

[52] U.S. Cl............................... 424/1; 252/301.1 R
[51] Int. Cl.² ..................... A61K 43/00; G21H 5/02
[58] Field of Search .................... 424/1; 423/2, 249; 252/301.1 R

[56] References Cited
UNITED STATES PATENTS
3,852,414   12/1974   Adler et al.............................. 424/1

OTHER PUBLICATIONS
Subramanian et al., Radiology, vol. 99, No. 1, Apr. 1971, pp. 192–196.

Primary Examiner—Benjamin R. Padgett
Assistant Examiner—Christine M. Nucker
Attorney, Agent, or Firm—Wenderoth, Lind & Ponack

[57] ABSTRACT

Aqueous fluids for skeletal imaging comprise technetium-99m present as a bone-seeking technetium-99m/tin/phosphate complex, are prepared using a monofluorophosphate and stannous fluoride or chloride, the molar proportion of monofluorophosphate to stannous ion being from 30:1 to 500:1, to react with pertechnetate. Kits for skeletal imaging comprise mixture of monofluorophosphate with stannous ion for reaction with pertechnetate.

7 Claims, No Drawings

TECHNETIUM-99m-TIN-MONOFLUOROPHOSPHATE COMPLEX

This invention relates to aqueous fluids for skeletal imaging containing technetium-99m complexes, and particularly such complexes as have bone-seeking properties making them potentially useful as bone-scanning agents.

Prior to 1971, the major γ-emitting radionuclides for skeletal imaging were strontium-87m, strontium-85, and fluorine-18. All these radionuclides suffered from serious disadvantages. Strontium-87m is generator produced and has a short half-life, hence scanning takes place against a high blood background. Strontium-85 has a long half-life (65 days), hence the patient is subjected to a high radiation dose, and poor quality scans are obtained because of the limitation on injectable dose. Fluorine-18 is a good agent whose distribution is however limited by its short half-life (1.83 hours).

In April 1971, G. Subramanian and J. G. McAfee published in Radiology, Vol. 99, pages 192–196 "A New Complex of Technetium-99m for Skeletal Imaging" describing an agent prepared by reduction of Technetium-99m with stannous chloride and complexing with tripolyphosphate. The labelled complex gave good skeletal uptake of activity but suffered from several disadvantages, the most important of which were a 24 hour delay before scanning which meant an injection of 16 times the Tc-99m activity required for adequate instrument response, and the instability of the long chain polyphosphate material with respect to hydrolysis.

The excellent physical characteristics (half life of 6 hours and monoenergetic gamma emission of 140 KeV with an external photon yield of 90%) of the readily available nuclide technetium-99m are well known. By virtue of its optimum half life and absence of β-emission, technetium-99m, can be administered in relatively large doses (10-15 mCi) without exceeding reasonable radiation levels. Technetium-99m had been used extensively in radioisotopic imaging procedures for almost every major organ in man, with the exception (until the discovery by Subramanian and McAfee) of the skeleton.

Since April 1971, bone-scanning agents based on technetium-99m have been the subject of worldwide interest. A lot of research work has been done to overcome the disadvantages of the original formulation of Subramanian and McAfee; there have been papers, and international conferences on the subject; and by February 1973, there were at least three commercially available bone-scanning agents based on technetium-99m/phosphate on the market.

The standard preparation of the bone-scanning agent according to these procedures starts from an aqueous solution of pertechnetate ion obtained as the eluate from a molybdenum-99 generator. This is reacted in aqueous solution with a stannous salt, generally a stannous chloride, to reduce the technetium to the $4^+$ state, and with a phosphate to form an anionic bone-seeking technetium-99m/tin/phosphate complex. (A variety of phosphates has been tried, generally in a molar excess over the stannous salt, to overcome the disadvantages of the tripolyphosphate proposed by Subramanian and McFee). The resulting aqueous solution, after pH adjustment if required, can be injected directly into the animal or human being, a skeletal image being obtainable a matter of hours later.

In their original paper of April 1971, Subramanian and McAfee mentioned in passing that they tried technetium complexes of fluorophosphate, but found their skeletal localization unsatisfactory; they therefore limited their teaching to the use of tripolyphosphate. The present invention is based on the unexpected discovery that under some circumstances the use of fluorophosphate can be advantageous. Indeed, we have obtained, using fluorophosphate, bone-scanning agents with properties equal to or better than any currently available on the market.

The particular conditions which we have found necessary in order to achieve success with fluorophosphate may be summarised as follows:

A. We use a water-soluble monofluorophosphate. Fluorophosphates containing any number of fluorine atoms from 1 to 6 are available, and it is not clear which Subramanian and McAfee may have used.

B. We prefer to use stannous fluoride as the stannous salt. Subramanian and McAfee do not mention stannous fluoride. Stannous fluoride is more stable to hydrolysis in aqueous solution than stannous chloride. Avoidance of hydrolysis is important, since solid hydrolysis products are taken up by the liver rather than by bones, and spoil the skeletal image.

C. While we do contemplate the use of stannous chloride as the stannous salt, we prefer to mix the solid stannous chloride with solid monofluorophosphate before dissolving the mixture in water, since we have found that precipitation of solid hydrolysis products can be avoided in this way without the necessity of using acid solutions. Subramanian and McAfee mix an acid solution of stannous chloride with pertechnetate solution, and then add phosphate, with the result that they require a subsequent addition of alkali to neutralise their solution.

D. We prefer to use a molar ratio of monofluorophosphate to stannous salt of from 50:1 to 110:1, since we have found that mixtures with ratios in this range have the highest biological efficiency. Subramanian and McAfee teach the use of tripolyphosphate and stannous chloride in a molar ratio not greater than 46:1.

E. We use a molar concentration of monofluorophosphate in the bone scanning agent of at least 0.05, because we have found that solutions at lower concentrations have a lower biological efficiency, particularly after storage. This lower scanning efficiency may be due to destruction of the monofluorophosphate by phosphatase enzyme action after injection. Subramanian and McAfee teach the use as bone-scanning agents of solutions containing a molar concentration of tripolyphosphate between about 0.015 or about 0.029.

F. We have found that sodium monofluorophosphate from commercial sources often contains significant quantities of free fluoride ion as an impurity, and that this free fluoride ion can reduce the efficiency of the Tc-99m skeletal imaging agent. We prefer to use a sodium monofluorophosphate containing no more than 5%, by weight measured as sodium fluoride, of free fluoride ion. It is not known what quality of fluorophosphate Subramanian and McAfee may have used.

The present invention provides in one aspect as aqueous fluid for skeletal imaging, containing in solution:

a. technetium-99, present as a bone-seeking technetium-99m/tin/monofluorophosphate complex, and present in a sufficient amount to provide a satisfactory skeletal image on injection into a mammal, b. tin, in a molar concentration of at least 0.0005 and c. monofluorophosphate, in a molar concentration of from 0.05 to 0.3, the molar ratio of monofluorophosphate to tin being from 30:1 to 500:1.

The present invention provides in another aspect a method of forming the aqueous fluid for skeletal imaging defined above, which method comprises reacting technetium-99m in the form of pertechnetate ion in aqueous solution with a mixture of a stannous halide with a water-soluble monofluorophosphate, the amounts concentrations and proportions being as defined above, until a bone-seeking technetium-99m/tin/-monofluorophosphate complex has been formed.

The pH of the resulting aqueous fluid will generally be from 5.5 to 6.5, so that no pH adjustment will normally be required. Adjustment of pH may be achieved, if necessary, by conventional methods.

The water-soluble monofluorophosphate may have any non-toxic cation, for example an alkali-metal cation. Sodium monofluorophosphate is readily and cheaply available and is the preferred material. As stated above, the molar concentration of the monofluorophosphate in the aqueous fluid for skeletal imaging needs to be at least 0.05; we believe that this may be required to avoid the danger of decomposition by phosphatase enzyme action. The upper limit on monofluorophosphate concentration of 0.3 M is not so critical; but we have found no advantage in going above this limit, while the problem of toxicity becomes increasingly severe at higher concentrations.

Sodium monofluorophosphate from commercial sources frequently contains impurities, the nature and extent of which probably depend on its process of manufacture. In particular, as stated above, the large quantities of free fluoride ion which are sometimes present can harm the skeletal imaging properties of the aqueous fluid. Free fluoride in monofluorophosphate can be analysed by means of a fluoride ion specific electrode. Free fluoride is only one of several factors affecting the performance of the product; tolerable skeletal imaging properties can be obtained in the presence of quite large amounts of free fluoride, provided that all the other conditions are right. Nevertheless we prefer to use a sodium monofluorophosphate containing no more than 5%, particularly no more than 2%, by weight measured as sodium fluoride, of fluoride ion.

As stated above, the molar ratio of monofluorosphosphate to tin needs to be at least 30:1 in order that the aqueous fluid for skeletal imaging may be stable and may have a high biological efficancy. The upper limit on this ratio of 500:1 is not so critical; but it is difficult to go beyond this ratio without using rather high concentrations of monofluorophosphate. The preferred range of molar ratios is from 50:1 to 110:1.

It is preferred that the molar concentration of stannous fluoride or stannous chloride in the aqueous mixture to be reacted, and of tin in the resulting aqueous fluid for skeletal imaging, be from 0.0005 to 0.0025. The stannous salt used may be anhydrous or hydrated.

When a stannous chloride is used as the stannous salt, we regard it as desirable to mix the solid stannous chloride with the solid monofluorophosphate. The solid mixture may then be dissolved or added directly to the aqueous pertechnetate solution.

When stannous fluoride is used as the stannous salt, these precautions do not appear to be necessary. In this case, the two components of the reaction mixture may be mixed together in any manner. The mixture of stannous fluoride and monofluorophosphate may be used as solid or solution.

Reaction between the pertechnetate, the stannous salt and the monofluorophosphate may conveniently be effected by holding the aqueous mixture at ambient temperature for at least 10 seconds with shaking or stirring. The formation of the desired technetium-99m tin/monofluorophosphate complex takes place quickly and easily, and the reaction conditions are not critical.

Existing bone-scanning kits based on technetium-99m comprise a mixture of a tin salt with a phosphate to be activated by the addition of an aqueous pertechnetate solution immediately prior to use. The present invention includes within its scope bone-scanning kits of this kind, and provides a bone-scanning kit comprising a vessel containing a mixture of:

a. stannous fluoride or stannous chloride, with b. a water-soluble monofluorophosphate, the molar ratio of (b) to (a) being from 30:1 to 500:1, the contents of the vessel being adapted, on addition of technetium-99m in the form of an aqueous solution of pertechnetate ion to form an aqueous solution of a bone-seeking technetium-99m/tin/monofluorophosphate complex.

Such a bone-scanning kit will generally comprise a plurality of such vessels each containing the stated mixture. This mixture may be present in the form of an aqueous solution; but aqueous solutions of stannous salts are not stable over extended periods, and it is therefore preferred that the mixture should be present as a solid.

To produce such a solid mixture, the solid components (a) and (b) may be admixed as such, but this is not preferred, since the amounts involved are so small that it is difficult to ensure that an accurately metered portion of the mixture, of precisely the same chemical composition in each case, is delivered to each vessel. It is therefore preferred to dissolve components (a) and (b) in water or an organic solvent, to disperse a metered volume of the solution or solutions to each vessel, and to remove the liquid from each vessel by conventional means, for example, freeze-drying in the case of aqueous solutions, or evaporation in the case of organic solvents.

We prefer to use aqueous solutions for this purpose. In order to avoid oxidation of the stannous salt, we prefer to thoroughly purge the aqueous solution with nitrogen or other inert gas, and to maintain the freeze-dried solid away from an oxidizing atmosphere, e.g. either under nitrogen or under a vacuum. Suitable precautions can quite easily be taken to seal the freeze-dried solid into the vessel under the vacuum used for freeze-drying and in a sterile condition. The use of a puncturable re-sealable end cap enables the aqueous pertechnetate solution to be inserted into the vessel, and the aqueous fluid for skeletal imaging to be removed therefrom, without loss of sterility.

Sterilisation can be achieved either by carrying out the entire process in a sterile environment, or alternatively by submitting the vials containing freeze-dried product to sterilisation with a gamma dose of 2.5 MRad.

Commercial molybdenum-99 generators are often arranged to deliver a dose of pertechnetate ion in the form of 15–30 ml of eluate in isotonic saline. Bone-scanning kits according to the present invention, which are intended to be activated by about 5 ml of aqueous pertechnetate solution, preferably contain from 35 mg to 200 mg of sodium or other water-soluble monofluorophosphate and from 0.5 mg to 2.0 mg of stannous fluoride or chloride, measured as the anhydrous salt.

The amount of the resulting aqueous fluid that needs to be injected into a mammal for skeletal imaging purposes will depend on the radioactive concentration of the technetium-99m, and on the size of the mammal. For the purpose of scanning human beings, it is usual to use doses of the order of 10–15 mCi. An activity of this level is likely to be contained in 1–5 ml of eluate. Toxicity studies indicate that toxicity arising from the complex with monofluorophosphate in aqueous fluids according to this invention should not be a problem in human beings.

The following Examples illustrate the invention.

Stannous flouride or stannous chloride and sodium monofluorophosphate were dissolved in 100 ml of nitrogen-purged pyrogen-free water. The resultant solution was dispersed in 1 ml aliquots into sterile vials through a 0.22 micron Millipore filter and then freeze-dried. The quantities of stannous salt and monofluorophosphate were chosen to provide in each vial the weight of solid indicated in Table 1 below. Stannous chloride was mixed with the sodium monofluorophosphate before solution in Example 11. The contents of each vial were maintained in a sterile condition under nitrogen by means of a puncturable re-salable closure applied to each vessel.

Vials were activated by injecting 5 ml of technetium-99m pertechnetate solution in isotonic saline into each and gently shaking for about a minute. The resulting fluids were stable enough to be used throughout a working day, depending on the initial activity of the added technetium-99m. Portions of various vials were injected intravenously into the tail veins of male wistar rats of 100–200 g body weight in the conventional manner. The rats were sacrificed the stated number of hours after injection, and the activities in major organs were determined by counting multiple samples from each organ in a dual crystal scintillation counter. The results are set out in Table 1 below. The bone figures were calculated on the basis that the weight percentage of bone in these rats was 10%. A study of Table 1 indicates that Examples 2, 4 and 6 to 11 were successful, in that there was low liver and kidney uptake, and the activity ratios were satisfactory. Examples 3 and 5 were less successful, in that in Example 5 there was a higher kidney uptake and in both Examples the activity ratios were lower. In each case, the molar concentration of sodium monofluorophosphate was only 0.014; this is below the minimum of 0.05 specified for aqueous fluids for skeletal imaging of this invention. The molar ratio of sodium monofluorophosphate to stannous fluoride in Example 1, which was also a failure, was only 10.9, well below the minimum of 30 specified for aqueous fluids of this invention.

In Table II below the formulation of Example 4 has been compared to the three bone-scanning kits currently available. The tests were all performed on male wistar rats as described above. Dissection times used were those recommended in the instructions supplied with the kits. The instructions provided with each commercial kit were followed exactly.

Commercial Kit A gave rise to a rather high kidney uptake, and the bone uptake and bone/muscle ratio were not as high as with Example 4. Furthermore, the recommended scanning time for this kit is 3–5 hours after injection, whereas the optimum scanning time for Example 4 is about 2 hours after injection. The results given in the Table were obtained 5 hours after injection; the figures after 3 hours were even less good.

Commercial Kit B gave rise to an intolerably high liver uptake, which did not drop significantly during 4 hours after injection.

Commercial Kit C gave results nearly as good as those of Example 4. However, the recommended scanning time for Kit C is 3 to 4 hours. Results obtained after 2 and 4 hours after injection were not significantly different.

The stated toxicity of Kit C is 150 mg/kg LD 50/30 days in mice. The preparation of Example 4 of the present invention is not toxic to male T.O. mice at dose levels of 350 mg/kg of $Na_2PO_3F$ and 3.5 mg of $SnF_2$. It is therefore believed that the toxicity of the Example 4 formulation is less than half that of Kit C, which is based on a polyphosphate.

In clinical trials of the invention, 126 patients with known primary cancers were treated by injecting them with the aqueous fluid of Example 4. The patients were then subjected to skeletal scans for detection of possible secondary tumours in bones. 56 cases of secondary tumours were found, only 24 of which had been previously observed by standard x-ray radiography techniques. No adverse reaction to the aqueous fluid was observed in any of the patients.

TABLE I

| Example No | 1 | 2 | 3 | 4 | 5 | 6 | 7 | 8 | 9 | 10 | 11 |
|---|---|---|---|---|---|---|---|---|---|---|---|
| $Na_2PO_3F$ (mg) | 10 | 100 | 10 | 100 | 10 | 50 | 100 | 200 | 100 | 200 | 100 |
| $SnF_2$ (mg) | 1.0 | 3.0 | 0.2 | 2.0 | 0.1 | 0.5 | 1.0 | 2.0 | 0.5 | 0.5 | 0 |
| $SnCl_2.2H_2O$ (mg) | 0 | 0 | 0 | 0 | 0 | 0 | 0 | 0 | 0 | 0 | 1.5 |
| Molar Ratio $PO_3F^{2-}$ : $Sn^{2+}$ | 10.9 | 36.3 | 54.5 | 54.5 | 109 | 109 | 109 | 109 | 218 | 436 | 109 |
| No of animals tested | 3 | 3 | 9 | 9 | 2 | 2 | 26 | 3 | 4 | 3 | 3 |
| Dissection time (hrs since inj") | 2 | 2 | 2 | 2 | 2 | 2 | 2 | 2 | 2 | 2 | 2 |
| % injected dose in : | | | | | | | | | | | |
| Liver | 91.3 | 2.8 | 1.2 | 2.3 | 1.8 | 1.3 | 0.96 | 1.7 | 1.6 | 1.0 | 0.6 |
| Kidney | — | 5.2 | 3.6 | 3.9 | 9.3 | 3.7 | 4.1 | 4.4 | 4.9 | 3.5 | 4.2 |
| Muscle | — | 3.7 | 6.1 | 3.0 | 5.7 | 4.3 | 5.4 | 3.8 | 3.8 | 3.8 | 4.2 |
| Bone | <10.0 | 47.5 | 47.4 | 45.6 | 28.2 | 42.6 | 44.3 | 47.2 | 45.1 | 43.4 | 44.7 |
| Blood | — | 2.5 | 2.8 | 1.5 | 4.1 | 2.2 | 1.98 | 2.2 | 2.8 | 2.0 | 2.1 |
| Ratio of % injected dose per 1% body weight in : | | | | | | | | | | | |
| Bone/blood | — | 10.1 | 9.5 | 16.8 | 3.5 | 10.0 | 13.2 | 10.9 | 8.7 | 11.6 | 11.2 |
| Bone/muscle | — | 56.2 | 36.6 | 67.2 | 19.2 | 43.3 | 41.4 | 53.2 | 51.3 | 52.5 | 44.4 |
| Bone/tissue | — | 36.2 | 38.8 | 49.9 | 21.9 | 39.4 | 42.8 | 41.2 | 43.3 | 42.4 | 29.2 |

TABLE II

|  | Commercial Kit A | Commercial Kit B | Commercial Kit C | Kit of Example 4 |
|---|---|---|---|---|
| Number of animals tested | 7 | 8 | 6 | 9 |
| Dissection time (hrs after injection) | 5 | 1 | 2–4 | 2 |
| % injected dose in | | | | |
| Liver | 1.2 | 10.1 | 1.1 | 2.3 |
| Kidney | 10.6 | 1.6 | 1.8 | 3.9 |
| Muscle | 7.8 | 6.3 | 3.8 | 3.0 |
| Bone | 35.5 | 46.8 | 48.0 | 45.6 |
| Blood | 2.0 | 1.73 | 1.22 | 1.5 |
| Ratio of % injected dose per 1% body weight in | | | | |
| Bone/blood | 10.8 | 16.0 | 20.4 | 16.8 |
| Bone/muscle | 21.8 | 28.3 | 54.5 | 67.2 |
| Bone/tissue | 19.3 | 30.8 | 44.8 | 49.9 |

We claim:
1. Aqueous fluid for skeletal imaging, containing in solution:
   a. technetium-99m, present in a sufficient amount to provide a satisfactory skeletal image on injection into a mammal,
   b. tin, in a molar concentration of at least 0.0005 and
   c. monofluorophosphate, in a molar concentration of from 0.05 to 0.3, the molar ratio of monofluorophosphate to tin being from 30:1 to 500:1,
   said technetium-99m being present in combination with part of the tin and part of the monofluorophosphate as a bone-seeking technetium-99m/tin/-monofluorophosphate complex.

2. An aqueous fluid as claimed in claim 1, wherein the molar ratio of monofluorophosphate to tin is from 50:1 to 110:1.

3. A method of forming the aqueous fluid for skeletal imaging as claimed in claim 1, which method comprises reacting technetium-99m in the form of pertechnetate ion in aqueous solution with a mixture of stannous halide with a water soluble monofluorophosphate, the amounts and proprtions of the reactants being as defined in claim 1, until a bone-seeking technetium-99m/tin/monofluorophosphate complex has been formed.

4. A method as claimed in claim 3, wherein sodium monofluorophosphate is used as the monofluorophosphate.

5. A method as claimed in claim 4, wherein the sodium monofluorophosphate contains not more than 5%, by weight measured as sodium fluoride, of free fluoride ion.

6. A method as claimed in claim 3, wherein solid stannous chloride is mixed with solid sodium monofluorophosphate and the mixed reagent dissolved or added directly to the aqueous pertechnetate solution.

7. A method as claimed in claim 3, wherein stannous fluoride is used as the stannous halide and the components of the reaction mixture are mixed together in any desired manner.

* * * * *